United States Patent [19]

Brock et al.

[11] Patent Number: 5,705,663

[45] Date of Patent: Jan. 6, 1998

[54] QUATERNIZED TRIETHANOLAMINE DIFATTY ACID ESTERS

[75] Inventors: Michael Brock, Schermbeck; Meinolf Enneking, Herne; Kurt Kosswig, Marl, all of Germany

[73] Assignee: Servo Delden B.V., Delden, Netherlands

[21] Appl. No.: 568,569

[22] Filed: Dec. 7, 1995

[30] Foreign Application Priority Data

Dec. 23, 1994 [DE] Germany .............. 44 46 137.2

[51] Int. Cl.$^6$ .................................. C07C 101/00
[52] U.S. Cl. ................ 554/110; 554/103; 554/108; 554/109; 554/114; 564/281; 564/291; 564/292; 564/294; 564/296; 252/8; 510/515
[58] Field of Search ................ 554/114, 103, 554/110; 564/281, 291, 292, 294, 296; 252/8; 510/515

[56] References Cited

U.S. PATENT DOCUMENTS

| | | |
|---|---|---|
| 3,915,867 | 10/1975 | Kang et al. . |
| 4,830,771 | 5/1989 | Rubeck et al. .............. 252/8.8 |
| 5,443,631 | 8/1995 | Brock et al. . |
| 5,447,643 | 9/1995 | Kelkenberg et al. . |
| 5,482,636 | 1/1996 | Brock et al. . |

FOREIGN PATENT DOCUMENTS

| | | |
|---|---|---|
| 0 295385 | 12/1988 | European Pat. Off. . |
| 0 498050 | 8/1992 | European Pat. Off. . |
| 0 550 361 | 7/1993 | European Pat. Off. . |
| 0 604726 | 7/1994 | European Pat. Off. . |
| 42 43 701 | 6/1994 | Germany . |
| WO 91/01295 | 2/1991 | WIPO . |

*Primary Examiner*—Porfirio Nazario-Gonzalez
*Assistant Examiner*—Deborah D. Carr
*Attorney, Agent, or Firm*—Oblon, Spivak, McClelland, Maier & Neustadt, P.C.

[57] ABSTRACT

The invention relates to quaternized triethanolamine difatty acid esters prepared from triethanolamine, fatty acid, fatty acid ester and a quaternizing agent and to a process for their preparation and to their use. The quaternized triethanolamine difatty acid esters thus prepared can be used to produce particularly storage-, temperature- and viscosity-stable rinse cycle laundry softeners having a high active content.

11 Claims, No Drawings

QUATERNIZED TRIETHANOLAMINE DIFATTY ACID ESTERS

BACKGROUND OF THE INVENTION

1. Field of the Invention

The invention relates to quaternized triethanolamine difatty acid esters prepared from triethanolamine, fatty acid, fatty acid ester and a quaternizing agent, to a process for their preparation, and to their use in rinse cycle laundry softeners (fabric conditioners).

2. Discussion of the Background

Quaternized difatty acid esters of triethanolamine, especially quaternized triethanolamine ditallow fatty acid ester (hereinafter abbreviated to TEA-quat), are increasingly displacing the traditional ditallowdimethylammonium chloride (DTDMAC) as active component in rinse cycle laundry softeners, since they have better ecotoxicological characteristics and excellent biodegradability (R. Puchta et al., 3rd CESIO World Surfactant Congress, London 1992, Proceedings Section D, p. 122). TEA-quat-treated textiles, especially natural fibers such as cotton, are better rewettable than those which have been treated with DTDMAC (WO 91/01295). In addition, the use of TEA-quats makes it possible to manufacture rinse cycle laundry softeners with active contents higher than those containing DTDMAC.

Quaternized triethanolamine fatty acid esters can be obtained by reacting triethanolamine with fatty acids (WO 91/01295 and also patent applications cited therein) or fatty acid esters and subsequent quaternization of the resulting triethanolamine fatty acid esters. The fatty acid used is usually tallow fatty acid (unhydrogenated or partially hydrogenated), while tallow, i.e. tallow fatty acid triglyceride (EP 0 284 036) or tallow fatty acid methyl ester (U.S. Pat. No. 3,915,867) is used as fatty acid ester. Dimethyl sulphate is the usual quaternizing agent. Of particular importance are products which are obtained by reacting triethanolamine with about 2 equivalents of a tallow fatty acyl radical and subsequent quaternization. The product is in fact a mixture of quaternized mono-, di- and triesters of triethanolamine and unconverted triethanolamine. This mixture is to be understood as meaning a quaternized triethanolamine di(tallow)fatty acid ester in the wider sense.

It is known that quaternized triethanolamine difatty acid esters based on oleic acid are as thin-liquid as rinse cycle softener concentrates prepared therefrom, but have no textile-softening effect (U.S. Pat. No. 3,915,867). On the other hand, the textile-softening effect of analogous compounds based on a saturated, i.e. hydrogenated, tallow fatty acid is very marked (DE 16 19 058 or DE 17 94 068), but only low strength rinse cycle laundry softener concentrates can be prepared therefrom. The market compromise is therefore the production of TEA-quats from partially hydrogenated tallow fatty acid, which, however, are only useful for preparing storage- and viscosity-stable rinse cycle laundry softeners with active contents of up to 20% by weight.

Yet the marketing and use of concentrated rinse cycle laundry softeners has the following advantages for manufacturers and consumers over dilute formulations:

Lower weight and volume to be transported,
Reduced filling costs,
Enlarged manufacturing capacity, and
Reduced packaging waste.

Increased efforts are therefore underway today to develop rinse cycle laundry softener concentrates.

A rinse cycle laundry softener has to meet the following requirements for successful market placement:

High storage stability
High temperature stability,
High viscosity stability, and
High color stability.

The rinse cycle laundry softener must have a guaranteed storage stability of several weeks in which no signs of separation may appear. Even large temperature fluctuations must not affect the consistency of the rinse cycle fabric softener. This holds both for the viscosity within a suitable range and also for the color.

These requirements are met only to a limited extent even by rinse cycle laundry softeners which contain TEA-quat. This holds in particular for formulations having a TEA-quat content of more than 20% by weight. They turn into a thick liquid within a few days, in the event of strong temperature fluctuations and in certain circumstances are no longer flowable.

It is an object of the present invention to provide quaternized triethanolamine difatty acid esters with which it is possible to prepare even rinse cycle laundry softeners having active contents of above 20% by weight which are storage-, temperature- and viscosity-stable and have a textile-softening effect.

SUMMARY OF THE INVENTION

It has been found that, surprisingly, the stated object is achieved by quaternized triethanolamine difatty acid esters based on fatty acid/fatty acid ester mixtures.

The present invention accordingly provides quaternized triethanolamine difatty acid esters obtained by reacting triethanolamine with 1.5 to 2.5 equivalents of a mixture of 70 to 90% by weight of fatty acid and 10 to 30% by weight of fatty acid esters, each based on the total amount of fatty acid and fatty acid ester, and subsequent quaternization of the reaction product with a quaternizing agent, or by a separate reaction of triethanolamine with 1.5 to 2.5 equivalents of fatty acid and 1.5 to 2.5 equivalents of fatty acid ester and mixing the respectively obtained triethanolamine difatty acid esters in a weight ratio of triethanolamine difatty acid ester from fatty acid, to triethanolamine difatty acid ester from fatty acid ester of from 70 to 90%:10 to 30% before quaternization and subsequent quaternization, or by separate reaction of triethanolamine with 1.5 to 2.5 equivalents of fatty acid and 1.5 to 2.5 equivalents of fatty acid ester and quaternization with a quaternizing agent and mixing in a weight ratio of quaternized fatty acid esters from fatty acid to quaternized fatty acid ester from fatty acid ester of 70 to 90%:10 to 30%.

The present invention further provides a process for preparing quaternized triethanolamine difatty acid esters from triethanolamine, fatty acid, fatty acid ester and a quaternizing agent, characterized in that either triethanolamine is reacted with 1.5 to 2.5 equivalents of a mixture of 70 to 90% by weight of fatty acid and 10 to 30% by weight of fatty acid ester, each based on the total amount of fatty acid and fatty acid ester, and the reaction product is subsequently quaternized, or in that triethanolamine is separately reacted with 1.5 to 2.5 equivalents of fatty acid and fatty acid ester and the respectively obtained triethanolamine difatty esters are then mixed before quaternization in a weight ratio of 70 to 90%: 10 to 30% and subsequently quaternized, or in that triethanolamine is separately reacted with 1.5 to 2.5 equivalents of fatty acid and fatty acid ester and, after the respective quaternization, mixed in a weight ratio of 70 to 90%:10 to 30%.

The present invention furthermore provides for the use of the quaternized triethanolamine difatty acid esters thus prepared in rinse cycle laundry softeners.

DETAILED DESCRIPTION OF THE PREFERRED EMBODIMENTS

Particularly suitable TEA-quats are prepared as follows:

1. Reaction of triethanolamine with 1.5 to 2.5, preferably 1.5 to 2.2, in particular 1.5 to 1.9, equivalents of a mixture consisting of 70 to 90% by weight of fatty acid and 10 to 30% by weight of fatty acid ester, each based on the total amount of fatty acid and fatty acid ester, and subsequent quaternization.

2. Separate reaction of triethanolamine with in each case 1.5 to 2.5, preferably 1.5 to 2.2, in particular 1.5 to 1.9, equivalents of fatty acid (batch 1) or fatty acid ester (batch 2) to form triethanolamine difatty acid esters. The two batches are combined so that the mixture consists of 70 to 90% by weight of batch 1 and 10 to 30% by weight of batch 2. This mixture is then quaternized.

3. Separate reaction of triethanolamine with in each case, 1.5 to 2.5, preferably 1.5 to 2.2, in particular 1.5 to 1.9, equivalents of fatty acid (batch 3) and fatty acid ester (batch 4) to form triethanolamine difatty acid esters and separate quaternization. The two batches are combined so that the mixture consists of 70 to 90% by weight of the TEA-quat of batch 3 and 10 to 30% by weight of the TEA-quat of batch 4.

In a preferred embodiment, the mixture of quaternized triethanolamine difatty acid esters consists of 72 to 80% by weight of fatty acid and 20 to 28% by weight of fatty acid ester, each based on the total amount of fatty acid and fatty acid ester. Such a mixture can be prepared by any of the above-mentioned methods 1., 2. or 3.

The triethanolamine difatty acid esters and the TEA-quats according to 1. to 3. are prepared under the customary reaction conditions known per se (WO 91/01295, U.S. Pat. No. 3,915,867, EP 0 284 036 and EP-B 0 295 385).

The fatty acids to be used according to the present invention can be of natural or synthetic origin. It is convenient to use those which contain 6 to 24, preferably 8 to 22, in particular 10 to 20, carbon atoms. The fatty acids of natural origin are derived for example from olive oil, sunflower oil, palm oil, rape seed oil, castor oil, sesame oil, tallow, fish oil, etc., in which case their hydrogenated or partially hydrogenated derivatives also find utility. Further fatty acids from which the quaternized triethanolamine difatty acid esters of the present invention can be prepared are capric acid, caprylic acid, caproic acid, lauric acid, myristic acid, palmitic acid, stearic acid, oleic acid, elaidic acid, linoleic acid, linolenic acid, behenic acid, erucic acid and castor oil acid. In the case of the fatty acids of synthetic origin, all aforementioned straight-chain components and also the branched-chain types are worth mentioning, for example those which stem from the oxo process, and also isostearic acid or else derivatives from the Guerbet condensation.

Particular preference is given to unhydrogenated and partially hydrogenated tallow fatty acid.

The fatty acid esters to be used according to the present invention stem from the fatty acids mentioned, the alcohols of the fatty acid esters being 1- to 6-hydric alcohols having 1 to 8, preferably 1 to 6, in particular 1 to 3, carbon atoms.

Particular preference is given to unhydrogenated and partially hydrogenated tallow fatty acid methyl ester.

The quaternization is customarily effected with conventional quaterinzation agents known to those of ordinary skill in the art, preferably with dimethyl sulphate, by conventional methods known to those of ordinary skill in the art.

The quaternized triethanolamine difatty acid esters are further processed according to the present invention into rinse cycle laundry softeners in mixtures with solvents. It is possible to use solvents as per formula I

$$C_1-C_4\text{—alkyl—OH} \qquad (I)$$

or formula II

$$HO-(CH_2-CHC)_a-H, \qquad (II)$$
$$\phantom{HO-(CH_2-}|$$
$$\phantom{HO-(CH_2-CH}R$$

where R=H, CH$_3$ and a=1 to 4, or alkoxylated natural oils and fats as described in DE-A 42 15 689 and EP-A 0 604 726.

Having generally described this invention, a further understanding can be obtained by reference to certain specific examples which are provided herein for purposes of illustration only and are not intended to be limiting unless otherwise specified.

EXAMPLES

The examples which follow illustrate the preparation and use of the present invention; they are not limiting in any sense.

The investigations of the below-recited examples are carried out using quaternized triethanolamine ditallow fatty acid esters (compounds 1 to 3) which differ in the raw materials base used:

Compound 1: product of the reaction of partially hydrogenated tallow fatty acid (carbon chain distribution of the acyl radicals: see Table 1) with triethanolamine (degree of esterification: 1.5) and subsequent quaternization with dimethyl sulphate. Compound 1 is present as a mixture in 10% by weight of isopropanol.

Compound 2: product of the reaction of unhydrogenated tallow fatty acid methyl ester (carbon chain distribution of the acyl radicals: see Table 1) with triethanolamine (degree of esterification: 1.5) and subsequent quaternization with dimethyl sulphate. Compound 2 is present as a mixture in 10% by weight of isopropanol.

Compound 3: product of the reaction of partially hydrogenated tallow fatty acid methyl ester (carbon chain distribution of the acyl radicals: see Table 1) with triethanolamine (degree of esterification: 1.5) and subsequent quaternization with dimethyl sulphate. Compound 3 is present as a mixture in 10% by weight of isopropanol.

TABLE 1

Carbon chain distribution of the acyl radicals in compounds of 1 to 3 (in % by weight of total acyl)

| Acyl | Compound | | |
|---|---|---|---|
| | 1 | 2 | 13 |
| $C_{14}$ | 3 | 1 | 1 |
| $C_{16}$ | 28 | 25 | 28 |
| $C_{16}$-ene | 2 | 3 | 2 |
| $C_{18}$ | 29 | 8 | 31 |
| $C_{18}$-ene | 37 | 55 | 37 |
| $C_{18}$-diene | 1 | 9 | 1 |
| Proportion of unsaturated acyl | 40 | 67 | 40 |

Compounds 1 and 2 are mixed with each other in the following weight ratios:

Mixture 1: 100% of compound 1;
Mixture 2: 75% of compound 1 and 25% of compound 2;
Mixture 3: 67% of compound 1 and 33% of compound 2;
Mixture 4: 50% of compound 1 and 50% of compound 2;
Mixture 5: 100% of compound 2.

For preliminary orientation, each of the 5 mixtures is used to prepare a rinse cycle laundry softener having an active content of 20% by weight for rheological studies. The following recipe is used (in % by weight):

| | |
|---|---|
| Mixture 1 to 5 | 22.2 |
| 25% strength aqueous CaCl$_2$ solution | 1.2 |
| Perfume | 0.4 |
| Water to 100% by weight | |

The viscosities of the rinse cycle laundry softeners are subsequently determined directly following preparation and after 2 weeks storage at 25° C., using a Brookfield viscometer at 25° C.

| | Rinse cycle laundry softener based on mixture | | | | |
|---|---|---|---|---|---|
| | 1 | 2 | 3 | 4 | 5 |
| Viscosity at once [mPa · s] | 650 | 100 | 130 | 40 | 1100 |
| Viscosity after 2 weeks at 25° C. [mPa · s] | — | 160 | — | — | — |

The "-" entries indicate that the stated test conditions have caused the rinse cycle laundry softener to become either inhomogeneous or so highly viscous that the viscosity cannot be determined.

The rinse cycle laundry softener based on mixture 5 is very highly viscous immediately following preparation. On storage this rinse cycle laundry softener thickens to such an extent that the viscosity can no longer be determined. This is surprising since in mixture 5 (=compound 2) the rinse cycle laundry softener contains the highest proportion of unsaturated acyl of all mixtures. The result is consequently contrary to the general expectation that a higher proportion of unsaturated acyl in the TEA-quat, in contradistinction to a TEA-quat having a high proportion of saturated acyl, must automatically lead to rinse cycle laundry softeners having a lower viscosity. This can only be explained with the important fact that compound 2 was prepared starting from a methyl ester.

The rinse cycle laundry softener based on mixture 3 or 4 has a low viscosity immediately following preparation, but is not stable to storage. Inhomogeneities appear.

The rinse cycle laundry softener based on mixture 1 compound 1) has a high viscosity at the beginning and thickens markedly on storage.

The rinse cycle laundry softener based on novel mixture 2 (75% by weight of compound 1 and 25% by weight of compound 2) exhibits advantageous behavior in that it is still of a very low viscosity following 2 weeks, storage at 25° C. To be able to rule out that only the proportion of unsaturated acyl in mixture 2 is responsible for the good storage stability, a mixture 6 is prepared which is analogous to mixture 2 but contains compound 3 instead of compound 2. Mixture 6 thus has the following composition:

Mixture 6: 75% by weight of compound 1 and 25% by weight of compound 3

This novel mixture 6 is examined alongside novel mixture 2 and mixture 1 in a further series of investigations to see whether it might not be possible to prepare therefrom also rinse cycle laundry softeners which retain their low viscosity and storage stability under tougher experimental conditions with active contents of 20, 25 and 30% by weight. Consequently 9 rinse cycle laundry softeners of the following composition are prepared:

With 20% by weight active content (in % by weight):

| | Rinse cycle laundry softener | | |
|---|---|---|---|
| | 1 | 2 | 3 |
| Mixture 1 | 22.2 | — | — |
| Mixture 2 | — | 22.2 | — |
| Mixture 6 | — | — | 22.2 |
| 25% strength aqueous CaCl$_2$ solution | 1.2 | 1.2 | 1.2 |
| Perfume | 0.4 | 0.4 | 0.4 |
| Water to 100% by weight | | | |

With 25% by weight active content (in % by weight):

| | Rinse cyale laundry softener | | |
|---|---|---|---|
| | 4 | 5 | 6 |
| Mixture 1 | 27.8 | — | — |
| Mixture 2 | — | 27.8 | — |
| Mixture 6 | — | — | 27.8 |
| 25% strength aqueous CaCl$_2$ solution | 3.2 | 3.2 | 3.2 |
| Perfume | 0.4 | 0.4 | 0.4 |
| Water to 100% by weight | | | |

With 30% by weight active content (in % by weight):

| | Rinse cycle laundry softener | | |
|---|---|---|---|
| | 7 | 8 | 9 |
| Mixture 1 | 33.3 | — | — |
| Mixture 2 | — | 33.3 | — |
| Mixture 6 | — | — | 33.3 |
| 25% strength aqueous CaCl$_2$ solution | 4.0 | 4.0 | 4.0 |
| Perfume | 0.5 | 0.5 | 0.5 |
| Water to 100% by weight | | | |

All 9 rinse cycle laundry softeners are subjected to a storage stability test in a conditioning cabinet. The storage stability is determined in the following 24 hour cycle over a period of 14 days in the "Prodicon" conditioning cabinet from Weiss Umwelttechnik GmbH: storing at 4° C. for 11.5 h, then heating to 40° C. over 30 minutes; storing at 40° C. for 11.5 hours and then cooling down to 4° C. over 30 minutes.

The storage stability is evaluated by determining the viscosity at 25° C. immediately following the preparation of the rinse cycle laundry softeners and also after 1 and 2 weeks, storage using a Brookfield viscometer (all measurements with a constant 6 rpm, so that spindle 1 is used at low viscosities and spindle 2 at high viscosities). A storage at 20° C. is carried out for the same period to ensure better comparability. The table below shows the viscosity values found (in mPa.s).

| Viscosity | Rinse cycle laundry softener | | | | | | | | |
|---|---|---|---|---|---|---|---|---|---|
| | 1 | 2 | 3 | 4 | 5 | 6 | 7 | 8 | 9 |
| At once | 650 | 100 | 70 | 350 | 60 | 120 | 1200 | 80 | 170 |
| After 1 week at 20° C. | 1930 | 100 | 40 | 520 | 70 | 80 | 2500 | 80 | 80 |
| After 2 weeks at 20° C. | — | 100 | 40 | 550 | 80 | 80 | — | 90 | 80 |
| After 1 week at 4°–40° C. | 2500 | 260 | 180 | 1440 | 60 | 70 | — | 150 | 170 |
| After 2 weeks at 4°–40° C. | — | 400 | 300 | 3400 | 130 | 80 | — | 400 | 370 |

The "—" entries indicate that the rinse cycle laundry softeners are so highly viscous that the viscosity cannot be determined.

A rinse cycle laundry softener is deemed marketable under the chosen experimental conditions when the viscosity is not more than 600 mPa.s after 2 weeks storage in the conditioning cabinet. Rinse cycle laundry softeners 1, 4 and 7, all prepared on the basis of mixture 1 (=compound 1), do not meet this condition. They are extremely storage-unstable. The situation is different with rinse cycle laundry softeners 2, 5 and 8, which were prepared from mixture 2. These are extremely storage-stable. This is not, as presumed, due to the higher proportion of unsaturated acyl in mixture 2, as testified by the likewise extremely good storage properties of rinse cycle laundry softeners 3, 6 and 9. These are based on mixture 6, which contains a similar proportion of unsaturated acyl to mixture 1. Thus, the high storage stability of rinse cycle laundry softeners based on mixture 2 or 6 is ascribable to the mixtures of 75% by weight of TEA-quat based on tallow fatty acid and 25% by weight of TEA-esterquat based on tallow fatty acid methyl ester.

The color stability and the textile softening effect of mixtures 2 and 6, and also of rinse cycle laundry softeners 2, 3, 5, 6, 8 and 9 prepared therefrom, do not differ from those of commercial TEA-quats or rinse cycle laundry softeners prepared therefrom.

Obviously, additional modifications and variations of the present invention are possible in light of the above teachings. It is therefore to be understood that within the scope of the appended claims, the invention may be practiced otherwise than as specifically described herein.

This application is based on German Patent Application P44 46 137.2 filed in the German Patent Office on Dec. 23, 1994, the entire contents of which are hereby incorporated by reference.

What is claimed as new and is desired to be secured by Letters Patent of the United States is:

1. A mixture of quaternized triethanolamine difatty acid esters comprising the combination of:
   A) 70–90% by wt. of the reaction product, which is quaternized, of triethanolamine with 1.5 to 2.5 equivalents of fatty acid; and
   B) 10–30% by wt. of the reaction product, which is quaternized, of triethanolamine with 1.5 to 2.5 equivalents of fatty acid esters, the percent by weight of each of A) and B) based on the total amount of reaction product of triethanolamine with fatty acid and of reaction product of triethanolamine with fatty acid ester.

2. The mixture of quaternized triethanolamine difatty acid esters of claim 1, wherein said fatty acids and a fatty acid radical of said fatty acid esters contain 6 to 24 carbon atoms.

3. The mixture of quaternized triethanolamine difatty acid esters of claim 1, wherein an alcohol of said fatty acid esters are 1- to 6-hydric alcohols having 1 to 8 carbon atoms.

4. The mixture of quaternized triethanolamine difatty acid esters of claim 1, wherein said fatty acid is tallow fatty acid or partially hydrogenated tallow fatty acid.

5. The mixture of quaternized triethanolamine difatty acid esters of claim 1, wherein said fatty acid ester is the methyl ester of tallow fatty acid or partially hydrogenated tallow fatty acid.

6. A rinse cycle laundry softener comprising the mixture of quaternized triethanolamine difatty acid esters of claim 1 and a solvent.

7. The rinse cycle laundry softener of claim 6, wherein said solvent is selected from the group consisting of
   (i) compounds of formula I

(ii) compounds of formula II

wherein R=H or $CH_3$ and a=1 to 4,
   (iii) alkoxylated natural oils and fats, and
   (iv) a mixture thereof.

8. A mixture of quaternized triethanolamine difatty acid esters obtained by:
   1) reacting triethanolamine with 1.5 to 2.5 equivalents of a mixture of 70 to 90% by weight of fatty acid and 10 to 30% by weight of fatty acid esters, each based on the total amount of fatty acid and fatty acid ester, and subsequent quaternization of the reaction product with a quaternizing agent, or
   2) a separate reaction of triethanolamine with 1.5 to 2.5 equivalents of fatty acid and fatty acid ester and mixing of the respectively obtained triethanolamine difatty acid esters before quaternization in a weight ratio of 70 to 90%:10 to 30% and subsequent quaternization; or
   3) a separate reaction of triethanolamine with 1.5 to 2.5 equivalents of fatty acid and fatty acid ester and quaternization with a quaternizing agent and mixing in a weight ratio of 70 to 90%:10 to 30%.

9. A process for preparing a mixture of quaternized triethanolamine difatty acid esters from triethanolamine, fatty acid, fatty acid esters and a quaternizing agent, comprising
   1) reacting triethanolamine with 1.5 to 2.5 equivalents of a mixture of:
      i) 70 to 90% by weight of fatty acid; and
      ii) 10 to 30% by weight of fatty acid ester, each based on the total amount of fatty acid and fatty acid ester; and 2) quaternizing the reaction product.

10. A process for preparing a mixture of quaternized triethanolamine difatty acid esters from triethanolamine, fatty acid, fatty acid esters and a quaternizing agent, comprising:

1) separately reacting triethanolamine with:
   i) 1.5 to 2.5 equivalents of fatty acid; and
   ii) 1.5 to 2.5 equivalents of fatty acid ester, 2) mixing the respectively obtained triethanolamine difatty acid esters in a weight ratio of triethanolamine difatty acid ester from fatty acid, to triethanolamine difatty acid ester from fatty acid ester of from 70 to 90%: 10 to 30%; and 3) quaternizing the mixture of step 2).

11. A process for preparing a mixture of quaternized triethanolamine difatty acid esters from triethanolamine, fatty acid, fatty acid esters and a quaternizing agent, comprising:

1) separately reacting triethanolamine with:
   i) 1.5 to 2.5 equivalents of fatty acid; and
   ii) 1.5 to 2.5 equivalents of fatty acid ester, 2) quaternizing each reaction mixture of step 1); and 3) mixing the respectively obtained quaternized triethanolamine difatty acid esters in a weight ratio of quaternized triethanolamine difatty acid ester from fatty acid, to quaternized triethanolamine difatty acid ester from fatty acid ester of from 70 to 90%: 10 to 30%.

* * * * *